United States Patent
McCoy

(10) Patent No.: US 10,064,790 B2
(45) Date of Patent: *Sep. 4, 2018

(54) HAIR CARE SOLID GRANULES THAT SUSTAIN ESSENTIAL OILS AND OR PLANT HERBAL EXTRACTS THAT EMULSIFY IN WATER CREATING THERAPEUTIC SOLUTION

(71) Applicant: Sarah Marie McCoy, Seattle, WA (US)

(72) Inventor: Sarah Marie McCoy, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,676

(22) Filed: Jun. 1, 2017

(65) Prior Publication Data

US 2017/0304158 A1 Oct. 26, 2017

Related U.S. Application Data

(63) Continuation-in-part of application No. 13/740,235, filed on Jan. 13, 2013, now Pat. No. 9,693,935.

(51) Int. Cl.
*A61K 8/02* (2006.01)
*A61K 8/92* (2006.01)
*A61K 8/98* (2006.01)
*A61Q 5/12* (2006.01)
*A61K 8/46* (2006.01)
*A61K 8/97* (2017.01)
*A61K 8/64* (2006.01)

(52) U.S. Cl.
CPC ............ *A61K 8/0225* (2013.01); *A61K 8/463* (2013.01); *A61K 8/64* (2013.01); *A61K 8/92* (2013.01); *A61K 8/97* (2013.01); *A61K 8/986* (2013.01); *A61Q 5/12* (2013.01); *A61K 2800/48* (2013.01); *A61K 2800/542* (2013.01); *A61K 2800/75* (2013.01); *A61K 2800/77* (2013.01)

(58) Field of Classification Search
None
See application file for complete search history.

*Primary Examiner* — Robert A Wax
*Assistant Examiner* — Randeep Singh

(57) ABSTRACT

A hair care product comprising 100% plant derived, biodegradable solid granules that sustain beneficial essential oils or herbal extracts that emulsify in water to create an emulsified therapeutic solution is disclosed. The hair care product improves over existing liquids in that its solid granule form is completely plant derived and biodegradable and can sustain essential oils and antioxidants without the requirement of chemical preservatives, and can be packaged in eco-friendly water soluble film and compostable paper. It improves over existing solid forms in that it is a 100% water soluble granule that emulsifies easily in water to form an easy to use liquid product.

6 Claims, 4 Drawing Sheets

HAIR CARE SOLID GRANULES THAT SUSTAIN ESSENTIAL OILS AND OR PLANT HERBAL EXTRACTS THAT EMULSIFY IN WATER CREATING THERAPEUTIC SOLUTION

REFERENCE TO RELATED APPLICATIONS

This patent application claims the benefit of U.S. Provisional Application No. 61/586,222 filed on Jan. 13, 2012, the disclosure of which is incorporated herein by reference in its entirety.

BACKGROUND OF THE INVENTION

Field of the Invention

The present invention relates to personal care product compositions, and more particularly to hair care product compositions in a granular solid form that do not require the addition of chemical preservatives, contains and sustains the therapeutic benefits of its components, utilizes greener packaging while retaining the familiar liquid form after reconstitution.

Description of Related Art

Current liquid personal care products require the addition of chemical preservatives. These chemical preservatives can be potentially irritating and are being shown to cause potential harm to the body.

The plastic bottles they come in pollute the environment. A solid form is more convenient to carry when traveling. However, the existing solid personal care products are not easy to use. Therefore there is a desire for greener, cleaner personal care products and such products still retain the convenience and characteristics of a familiar liquid form personal care product.

The present invention improves over existing liquids in that it's solid granule form can sustain therapeutic organic essential oils and antioxidants without the requirement of chemical preservatives. It improves on existing solid forms in that it uses 100% water soluble ingredients that emulsify easily in water to form an easy to use liquid product.

The claimed invention differs in its unique solid granule formula in that it contains and sustains the therapeutic benefit of organic essential oils and can contain color depositing plant/herbal extracts which would lose their ability to color the hair delivered in water. It can be packaged in water soluble film and PCR (Post Consumer Recycled) compostable paper as a solid and create a user friendly, eco-friendly solution.

SUMMARY OF THE INVENTION

One objective of the present invention is to provide a process for preparing hair care products which can circumvent the requirement of adding chemical preservatives that can be potentially irritating and are being shown to cause potential harm to the body.

Another object of the present invention is to provide a process for preparing hair care products which can make the product solid granular form to sustain therapeutic organic essential oils and antioxidants.

A further object of the present invention is to provide a process for preparing hair care products which improves over existing solid (solid form is more convenient to carry when traveling however existing solid forms are not easy to use) forms in that it is a 100% water soluble solid that can emulsify easily in hot or cold water to form an easy and familiar to use liquid product.

Still another object of the present invention is to provide a greener cleaner product. The present invention may be delivered in pre-measured water soluble film and packaged in PCR compostable paper as a solid and create a user friendly, eco-friendly solution.

A method of preparing hair care products according to the present invention comprises the steps of mixing plant derived, water soluble surfactants and other plant derived water-soluble emulsifiers/thickener in a container; adding conditioners, herbal extracts and essential oil/s, bacteria/mold protectors, and mixing the product until its uniform.

The products prepared this way can be packaged in PCR compostable paper and biodegradable water-soluble film and thus it provides a user-friendly, eco-friendly solution. Also it is convenient to carry a solid form hair care product onto the airplane, when traveling on the road, or camping. Moreover, the 100% water soluble granules can be reconstituted, dissolved and emulsified easily in hot or cold water to form an easy and familiar to use liquid product as conventional liquid form hair care products.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWING

Other aspects, features, and advantages of the present invention will become more fully apparent from the following detailed description, the appended claim, and the accompanying drawings in which similar elements are given similar reference numerals.

EMBODIMENT 1

Figure 1:
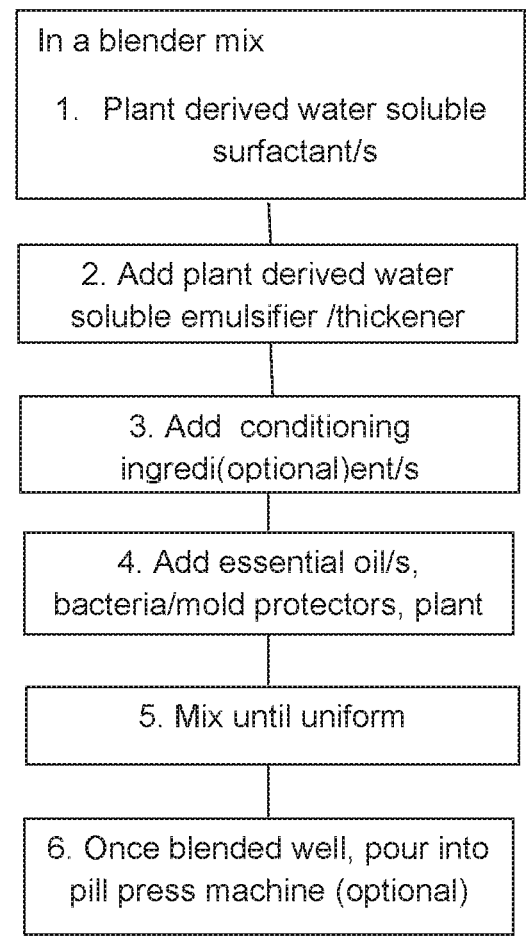
FIG. 1 is a flow chart showing how to make a conditioner according to one embodiment of the present invention.

Referring to FIG. 1, there is disclosed a flow chart on how to make a conditioner. In a container, blending plant derived water soluble surfactant/s 1; adding plant derived water soluble emulsifiers/thickener to the container 2; adding conditioning ingredient/s(optional) 3; adding at least one essential oil/herbal extract, bacteria/mold inhibitor 4; adding ph balancer 5; mixing/blending the product until it is uniform 6; pouring blended product into pill press machine (optional) 7. The granules' size of the product range from 150 mesh to 5 mm.

Figure 2:
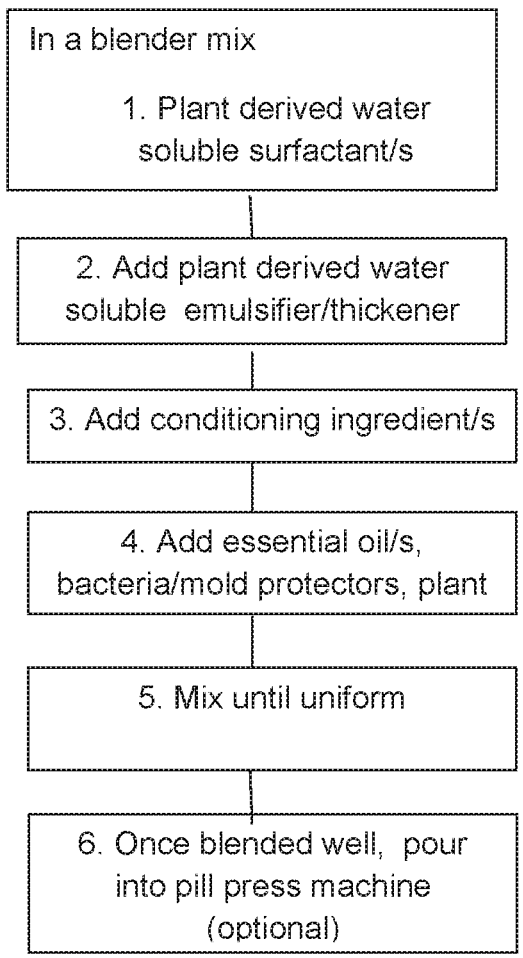
FIG. 2 is a flow chart showing how to make a shampoo according to one embodiment of the present invention.

Referring to FIG. 2, there is disclosed a flow chart on how to make a shampoo. In a container blending plant derived water soluble surfactant's 1; adding plant derived water soluble emulsifiers/thickener to the container 2; adding conditioning ingredient/s(optional) 3; adding at least one essential oil/herbal extract, bacteria/mold protectors 4; adding ph balancer 5; mixing/blending the product until it is uniform 6; pouring blended product into pill press machine (optional). 7. The granules' size of the product range from 150 mesh to 5 mm.

Figure 3:
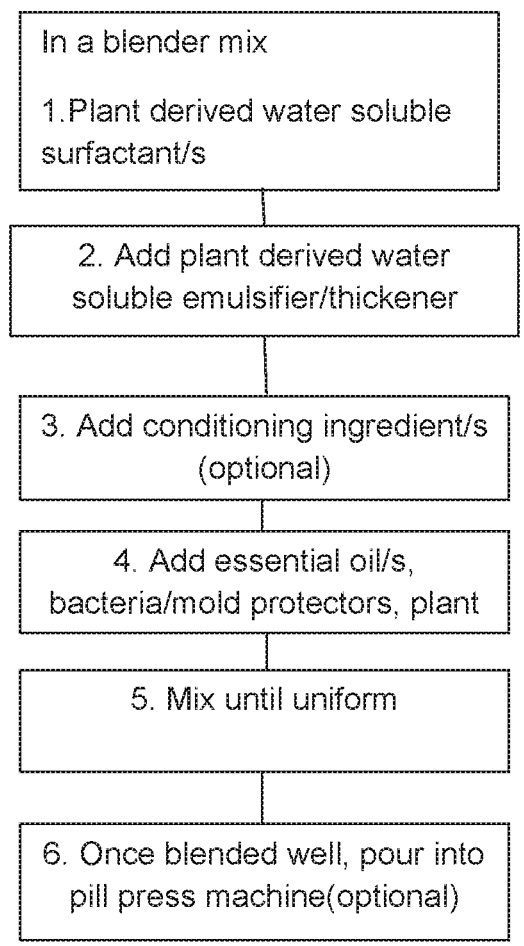
FIG. 3 is a flow chart showing how to make a hair coloring lotion according to one embodiment of the present invention.

Referring to FIG. 3, there is disclosed a flow chart on how to make a hair coloring lotion, In a container blending plant derived water soluble surfactant's 1; adding plant derived water soluble emulsifier/thickener to the container 2; adding conditioner(optional) 3; adding at least one herbal extract, bacteria/mold protectors 4; adding ph balancer 5; mixing/blending the product until it is uniform 6; pouring blended product into pill press machine(optional) 7. The granules size of the product range from 150 mesh to 5 mm.

More specifically, the solidifying water soluble plant-derived surfactant is selected from the group consisting of behentrimonium and salt thereof(ammonium), brassicamidopropyl dimethylamine and salts thereof(amine), stearyl dihydroxypropyldimonium oligosaccharides, sodium coco sulfate, sodium lauryl sulfate, sodium laureth sulfate, ammonium lauryl sulfate, ammonium laureth sulfate, sodium myristyl sulfate, sodium myreth sulfate, yucca extract, quillaja saponaria extract, sapindus mukorossi extract, shikakai extract, sodium lauroyl sarcosinate, sodium lauryl sulfoacetate, sodium cocoyl glycinate, sodium cocoyl/lauroyl glutamate, sodium cocoyl isethionate, sodium cocoyl/lauryl taurate, sodium C14-16 olefin sulfonate, diethylhexyl sodium sulfosuccinate, disodium lauryl sulfosuccinate, cocomidapropyl hydroxysultaine, cocomidapropyl betaine, brassicyl isoleucinate esylate, and the solidifying water soluble plant-derived surfactant is in an amount of 60.1-85% by weight of the product. The invention is not limited to the above listed surfactants.

The water soluble plant-derived emulsifier/thickener may be selected from the group consisting of guar gum in an amount of 6-20%, by weight of the product and preferably in an amount of 12% by weight of the product. The invention is not limited to the above listed emulsifier/thickeners.

The pH balancer including vinegar(powder), or citric acid in an amount of 4-12% by weight of the product, wherein the pH balancer is blended with the water soluble surfactant. The preferable amount of the pH balancer is 8% by weight of the product; the added amount is depending on the ph created by the other ingredients in the product. The invention is not limited to the above listed ph balancers.

The conditioning ingredient selected from the group consisting of cocoa butter, hydrolyzed plant proteins, peptides, amino acids, ceramides, panthenol, aloe vera leaf extract, or algae extract in an amount of 2-9% by weight of the product, wherein the conditioner is blended with the water soluble surfactant. The invention is not limited to the above listed conditioning ingredients.

The plant-derived antimicrobial ingredient in an amount of 1-4% by weight of the product, wherein the plant-derived antimicrobial ingredient including grapefruit seed extract, neem leaf extract, grape seed extract, or vinegar(powder). The invention is not limited to the above listed antimicrobial ingredients.

The plant-derived ingredient that can inhibit growth of mold and yeast in an amount of 1-4% by weight of the product, wherein the plant-derived anti-mold and anti-yeast ingredient including potassium sorbate, or vinega (powder). The invention is not limited to the above listed anti-mold and anti-yeast ingredients.

The essential oil and or herbal extract's selected from the group consisting of sweet orange, le ongrass, patchouli, sage, rosemary, peppermint, clove, cinnamon, lavender, frankincense, geranium, patchouli, juniper, thyme, tea tree, eucalyptus oil, and or at least one herbal extract selected from the group consisting of henna, indigo, cassia obovata, amla, neem, fenugreek, bhringraj, beet, or hibiscus extract (powders) in an amount of 2-25% by weight of the product, wherein the essential oil and or herbal extract is blended with the water soluble surfactant.

While the process outlined herein is in regard to shampoo related products such described process can also be employed with a facial or body wash formulation. Effectively, face/body wash, and face/body lotion, as well all lend themselves to this chemical composition formulation process.

Figure 4:
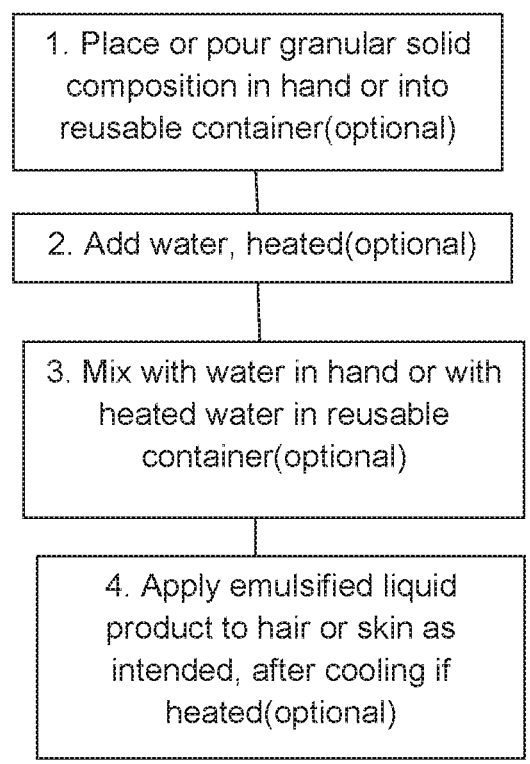
FIG. 4 is a flow chart showing how to use the hair care product according to the present invention.

Referring to FIG. 4, there is disclosed a method for applying an emulsified solution to hair/or skin of a person comprising: 1. placing granular solid composition in hand, or pouring/placing in reusable container(optional); 2. adding water, heated(optional); 3. mixing with water in hand or with heated water in container(optional) to form an emulsified solution; 4. wherein the newly formed liquid product, upon cooling if heated(optional), is what is applied externally to the hair or skin as the composition is intended for.

Additionally, this invention could be sold in larger bulk packaging to be used for refilling glass containers/bottles, smaller compostable paper packets or water-soluble film for single-use and travel.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed. Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

What is claimed is:

1. A hair care product having a water soluble granular emulsified solid composition for topical use after reconstitution, the product comprising: at least one solidifying water soluble plant-derived surfactant selected from the group consisting of anionic, cationic, nonionic, amphoteric surfactants, and a combination thereof; at least one water soluble plant-derived emulsifier/thickener; at least one plant-derived antimicrobial ingredient; at least one plant-derived anti-mold or anti-yeast ingredient; at least one essential oil or herbal extract; wherein the solidifying water soluble plant-derived surfactant is in an amount of 60.1-80% by weight of the product, the essential oil or herbal extract is in an amount of 2-10% by weight of the product, the antimicrobial ingredient is in an amount of 1-4% by weight of the product, and the anti-mold or anti-yeast ingredient is in an amount of 1-4% by weight of the product; wherein the ingredients of the hair care product are blended; and wherein the hair care product is packaged for reconstitution.

2. The hair care product of claim 1, wherein the solidifying water soluble plant-derived surfactant is selected from the group consisting of behentrimonium and ammonium salts thereof, stearamidopropyl dimethylamine and amine salts thereof, sodium coco sulfate, sodium lauryl sulfate, yucca extract, quillaja saponaria extract, sapindus mukorossi extract, shikakai extract, sodium lauryl sulfoacetate, sodium C-14/C-16 olefin sulphonate, sodium cocoyl glycinate, sodium cocoyl/lauroyl glutamate, sodium cocoyl isethionate, disodium lauryl sulfosuccinate, cocomidapropyl hydroxysultaine, cocomidapropyl betaine, and brassicylisoleucinate esylate.

3. The hair care product of claim 2, further comprising at least one pH balancer selected from the group consisting of powdered vinegar, citric acid, and lactic acid in an amount of 4-12% by weight of the product.

4. The hair care product of claim 3, further comprising at least one conditioning ingredient selected from the group consisting of cocoa butter, hydrolyzed protein, amino acids, peptides, ceramides, panthenol, aloe vera extract, and algae extract in an amount of 2-9% by weight of the product.

5. The hair care product of claim 4, wherein the water soluble plant-derived emulsifier/thickener is guar gum in an amount of 6-20% by weight of the product.

6. The hair care product of claim 5, wherein the at least one essential oil is selected from the group consisting of sweet orange, lemongrass, sage, rosemary, peppermint, clove, cinnamon, lavender, frankincense, geranium, juniper, thyme, tea tree, and eucalyptus oil, and the at least one herbal extract is selected from the group consisting of henna, indigo, cassia obovata, amla, neem, fenugreek, bhringraj, beet and powdered hibiscus extract.

* * * * *